US012669649B2

(12) United States Patent
Pisanello et al.

(10) Patent No.: US 12,669,649 B2
(45) Date of Patent: Jun. 30, 2026

(54) MICROFABRICATION TECHNIQUE FOR STRUCTURING NON-PLANAR ELECTROMAGNETIC WAVEGUIDES

(71) Applicant: FONDAZIONE ISTITUTO ITALIANO DI TECNOLOGIA, Genoa (IT)

(72) Inventors: Ferruccio Pisanello, Lecce (IT); Massimo De Vittorio, Lecce (IT); Marco Pisanello, Lecce (IT); Antonio Balena, Copertino (IT); Barbara Spagnolo, Corigliano d'Otranto (IT); Filippo Pisano, Lecce (IT); Marco Bianco, Maglie (IT); Leonardo Sileo, Calimera (IT)

(73) Assignee: FONDAZIONE ISTITUTO ITALIANO DI TECNOLOGIA, Genoa (IT)

( * ) Notice: Subject to any disclaimer, the term of this patent is extended or adjusted under 35 U.S.C. 154(b) by 375 days.

(21) Appl. No.: 18/573,182

(22) PCT Filed: Jun. 28, 2022

(86) PCT No.: PCT/IB2022/055986
§ 371 (c)(1),
(2) Date: Dec. 21, 2023

(87) PCT Pub. No.: WO2023/275737
PCT Pub. Date: Jan. 5, 2023

(65) Prior Publication Data
US 2024/0286954 A1 Aug. 29, 2024

(30) Foreign Application Priority Data
Jun. 29, 2021 (IT) ........................ 102021000017012

(51) Int. Cl.
*G02B 6/13* (2006.01)
*A61B 5/00* (2006.01)
(Continued)

(52) U.S. Cl.
CPC .............. *G02B 6/13* (2013.01); *A61B 5/0084* (2013.01); *A61B 5/293* (2021.01); *A61B 5/6868* (2013.01);
(Continued)

(58) Field of Classification Search
None
See application file for complete search history.

(56) References Cited

U.S. PATENT DOCUMENTS

2005/0232544 A1 10/2005 Blumberg
2018/0325379 A1 11/2018 Wolfe et al.

FOREIGN PATENT DOCUMENTS

WO 2015/008233 A1 1/2015
WO 2018/167685 A1 9/2018

OTHER PUBLICATIONS

B. Spagnolo et al., "Integrated tapered fibertrode for simultaneous control and readout of neural activity over small brain volumes with reduced light-induced artefacts", https://doi.org/10.1101/2020.07.31.226795; the version posted on Feb. 5, 2021. (Year: 2021).*
(Continued)

*Primary Examiner* — Jiong-Ping Lu
(74) *Attorney, Agent, or Firm* — CANTOR COLBURN LLP

(57) ABSTRACT

A method for manufacturing a multifunctional electromagnetic waveguide from a tapered optical fiber is provided. The method involves mounting the optical fiber on a roto-translational handling apparatus, forming a first mask on a tapered section of the optical fiber to define a shape of an optical window, forming a first metal layer around the
(Continued)

tapered section leaving a lateral edge of the first mask uncovered, removing the first mask by chemical etching to uncover the optical window, depositing a first transparent layer around the tapered section, depositing a second metal layer around the first transparent layer, forming a second mask that defines a shape of a conductive track, removing the second metal layer by chemical etching, and removing the second mask by chemical etching to uncover the conductive track.

5 Claims, 5 Drawing Sheets

(51) Int. Cl.

| | |
|---|---|
| *A61B 5/293* | (2021.01) |
| *C03C 25/1065* | (2018.01) |
| *G02B 6/12* | (2006.01) |
| *G02B 6/132* | (2006.01) |
| *G02B 6/136* | (2006.01) |

(52) U.S. Cl.
CPC ............ *C03C 25/1068* (2018.01); *G02B 6/12* (2013.01); *G02B 6/132* (2013.01); *G02B 6/136* (2013.01); *A61B 2562/0233* (2013.01); *A61B 2562/028* (2013.01); *A61B 2562/12* (2013.01); *A61B 2562/125* (2013.01); *G02B 2006/12085* (2013.01); *G02B 2006/12173* (2013.01); *G02B 2006/12176* (2013.01); *G02B 2006/12195* (2013.01)

(56) References Cited

OTHER PUBLICATIONS

A. Rizzo et al., "Laser micromachining of tapered optical fibers for spatially selective control of neural activity", Microelectronic Engineering, vol. 192, pp. 88-95. (Year: 2018).*

International Search Report for International Patent Application No. PCT/IB2022/055986, mailed Nov. 4, 2022.

Spagnolo B. et al., Integrated tapered fibertrode for simultaneous control and readout of neural activity over small brain volumes with reduced light-induced artefacts, BioRxiv, Feb. 5, 2021, DOI: 10.1101/2020.07.31.226795.

Sanyuan Chen et al., Paper, A fiber-based implantable multi-optrode array with contiguous optical and electrical sites, Journal of Neural Engineering, Jul. 24, p. 46020, 2013, vol. 10, No. 4, IOP Publishing, Bristol, GB.

Pisano F. et al., Focused ion beam nanomachining of tapered optical fibers for patterned light delivery, Microelectronic Engineering, Aug. 5, 2018, pp. 41-49 vol. 195, Elsevier.

Rizzo A. et al., Laser micromachining of tapered optical fibers for spatially selective control of neural activity, Microelectronic Engineering, May 15, 2018, pp. 88-95, vol. 192, Elsevier.

Balena A. et al., Two-photon fluorescence-assisted laser ablation of non-planar metal surfaces: fabrication of optical apertures on tapered fibers for optical neural interfaces, Optics Express, Jul. 20, 2020, pp. 21368-21381, vol. 28, Issue 15, Optica Publishing Group.

Written Opinion for International Patent Application No. PCT/IB2022/055986, mailed Nov. 4, 2022.

* cited by examiner

MICROFABRICATION TECHNIQUE FOR STRUCTURING NON-PLANAR ELECTROMAGNETIC WAVEGUIDES

CROSS-REFERENCE TO RELATED APPLICATIONS

This application is a National Phase Application of PCT International Application PCT/IB2022/055986, having an International Filing Date of Jun. 28, 2022 which claims priority to Italian Application No. 102021000017012 filed Jun. 29, 2021, each of which is hereby incorporated by reference in its entirety.

FIELD OF THE INVENTION

This invention relates in general to techniques for producing multifunctional electromagnetic waveguides from tapered optical fibers.

BACKGROUND OF THE INVENTION

The field of technologies for optical interfaces with the central nervous system has seen significant developments in the last 10 years, creating a need for implantable devices which are able to control and monitor the cellular activity in three dimensions and at a high spatial-temporal resolution. This has increased the need for new methods for manufacturing non-planar surfaces to be developed, in order to integrate elements for applying and monitoring the nerve activity along and around the implantation axis. In such a scenario, a micro-structuring approach (also known as "micro-patterning") which may be applied directly to highly curved surfaces or to multiple sides of a three-dimensional probe would be highly desirable, because it could pave the way for the production of implantable optoelectronic devices that have complex interaction geometries with the tissue around the implantation axis.

In this respect, tapered optical fibers (TF) have recently emerged as a promising platform for forming optical and electrical neural interfaces, with optical channels provided by the guided modes, and the possibility for the tapered surface that provides a non-planar surface ready for structuring to be coated with metal. The metal coating in fact aims to provide a reflective coating in order to obtain a waveguide confined by metal, while the structuring thereof may make it possible to use mode division multiplexing to obtain a selective distribution of light and the formation of electrical contacts. The TF are characterized by a tapered section extending over a length of >0.5 mm, with an initial diameter between 50 and 400 μm and a diameter at the tip of <1 μm (cf. the schematic view in FIG. 1A), and the mode division multiplexing properties thereof allow for light to be distributed in a manner resolved along the axis of the device and/or for light to be collected with depth resolution. However, forming electronic circuits and electric devices on the tapered section of the fiber is a challenge, since: (i) the tapered surface is non-planar, (ii) the radius of curvature thereof is small and reduces along the axis of the waveguide (FIG. 1B), and (iii) the fiber has to be structured over its 360° of symmetry. The methods for structuring the surface of the TF are limited to a few geometries and only allow for the formation of a single site for recording the electrical signal in order to monitor the electrical activity of the cells in the vicinity of the implant. These approaches include the use of focused ion beam (FIB) abrasion (milling) [1, 2], laser ablation [3, 4], and focused ion beam local deposition (FIBID) [1]. The latter makes it possible to locally deposit platinum on a metal layer and obtain an extracellular site for recording the electrical signal, but requires work to be carried out on a system that already has an electrical connection [1]. Moreover, the formation of two or more electrodes is restricted by the fact that each electrode would require an additional metal layer, which would generate capacitive coupling effects that would prevent the device from functioning correctly. A structuring approach that would make it virtually possible to form any bespoke geometry and multiple recording sites over 360° of the tapered surface would significantly increase the set of characteristics that may be integrated into the tapered section.

SUMMARY OF THE INVENTION

In view of this need, the invention relates to a method for manufacturing an electromagnetic waveguide from a tapered optical fiber, comprising the following steps:

mounting the optical fiber on a handling apparatus which may be actuated to translationally move the optical fiber along at least one translation axis and rotate the optical fiber about a longitudinal axis thereof, submerging a tapered section of the optical fiber in a photoresist and subjecting the photoresist to two-photon polymerization in order to form a first mask defining the shape of at least one optical window, subjecting the masked tapered section to a plurality of directional flows of metal material in order to form a first metal layer around the tapered section, leaving at least one lateral edge of the first mask uncovered, removing the first mask by chemical etching in such a way to uncover said at least one optical window, depositing a transparent, conformal first layer around the tapered section, said transparent, conformal first layer being made of insulating material, depositing a second metal layer around the insulating layer, submerging the tapered section in the photoresist and subjecting the photoresist to two-photon polymerization in order to form, at the tapered section, a second mask defining the shape of at least one conductive track, removing, by chemical etching, the second metal layer where the second metal layer is not covered by the second mask, and removing the second mask by chemical etching in such a way to uncover said at least one conductive track.

The method according to the invention achieves the following advantages:

possibility of creating optical and electrical channels using the same technological processes (conformal deposition of metals and insulators, two-proton polymerization, wet etching)

patterning of non-planar surfaces

360° patterning of a tapered waveguide that has a small, non-constant radius of curvature the method makes it possible to produce random arrangements of windows and electrodes on the tapered surface, including specific electrode geometries for the triangulation of the neural signal, or tetrodes. The method may be extended to the non-tapered part of the optical fiber the formation of electrodes around the implant allows for a three-dimensional electrophysiology analysis, for example by recording the electrical signals around the implant the possibility to produce electrodes all around the implant makes it possible to produce devices that may eliminate electric field shielding (EFS). EFS is typically present in the standard planar probes that have electrodes on just one side of the device, making it difficult to read the electrical signal of the cells positioned behind the device almost all of the steps of the method may be done in parallel, and therefore more fibers may be processed simultaneously it is possible to interface the three-dimensional waveguide with a standard two-dimensional device, by means of a dedicated printed circuit board.

BRIEF DESCRIPTION OF THE FIGURES

Further features and advantages of the method according to the invention will be presented in the following detailed description, which refers to the accompanying drawings, provided solely by way of non-limiting example, in which.

DETAILED DESCRIPTION

Figure 1:
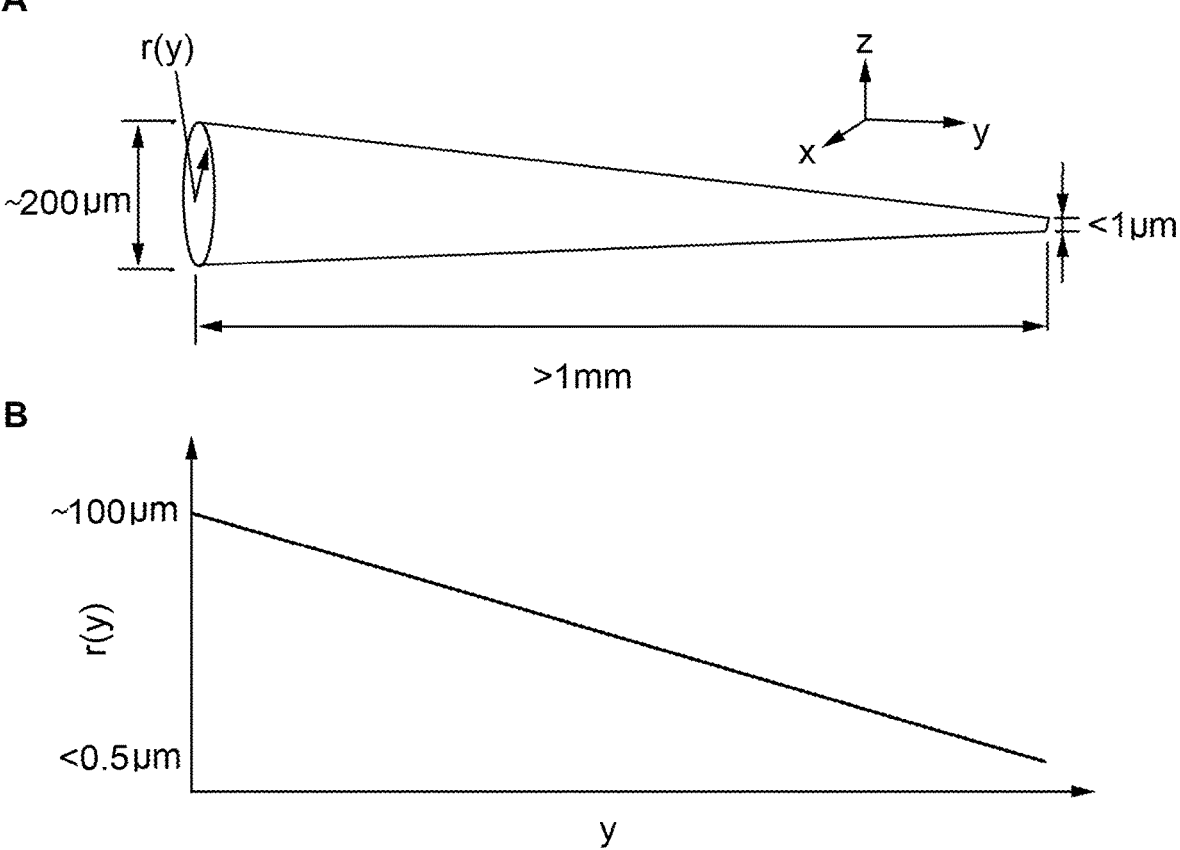
FIG. 1 shows: A-a schematic view of a tapered optical fiber covered with metal, B—the course of the radius of curvature of the tapered section r(y) along the direction of the axis of the fiber.

A method for producing an optoelectronic device based on tapered optical fibers, in particular an optoelectronic neural interface, will now be described. A device of this kind is described, for example, in WO 2015/008233 A1 and WO 2018/167685 A1, from the same applicant.

An example of this device is shown in FIG. 2, and essentially comprises two parts: a micro-structured implantable probe, which is denoted by reference sign 10 and comprises electrodes 11 for electrically recording the neural activity and optical windows 12 for allowing light to be emitted and collected in the cerebral tissue with depth resolution, and a printed circuit interface 20 which is used as an interface between the non-planar electronics on the probe 10 and a planar printed circuit board 30.

Figures 2A, 2B, 2C:
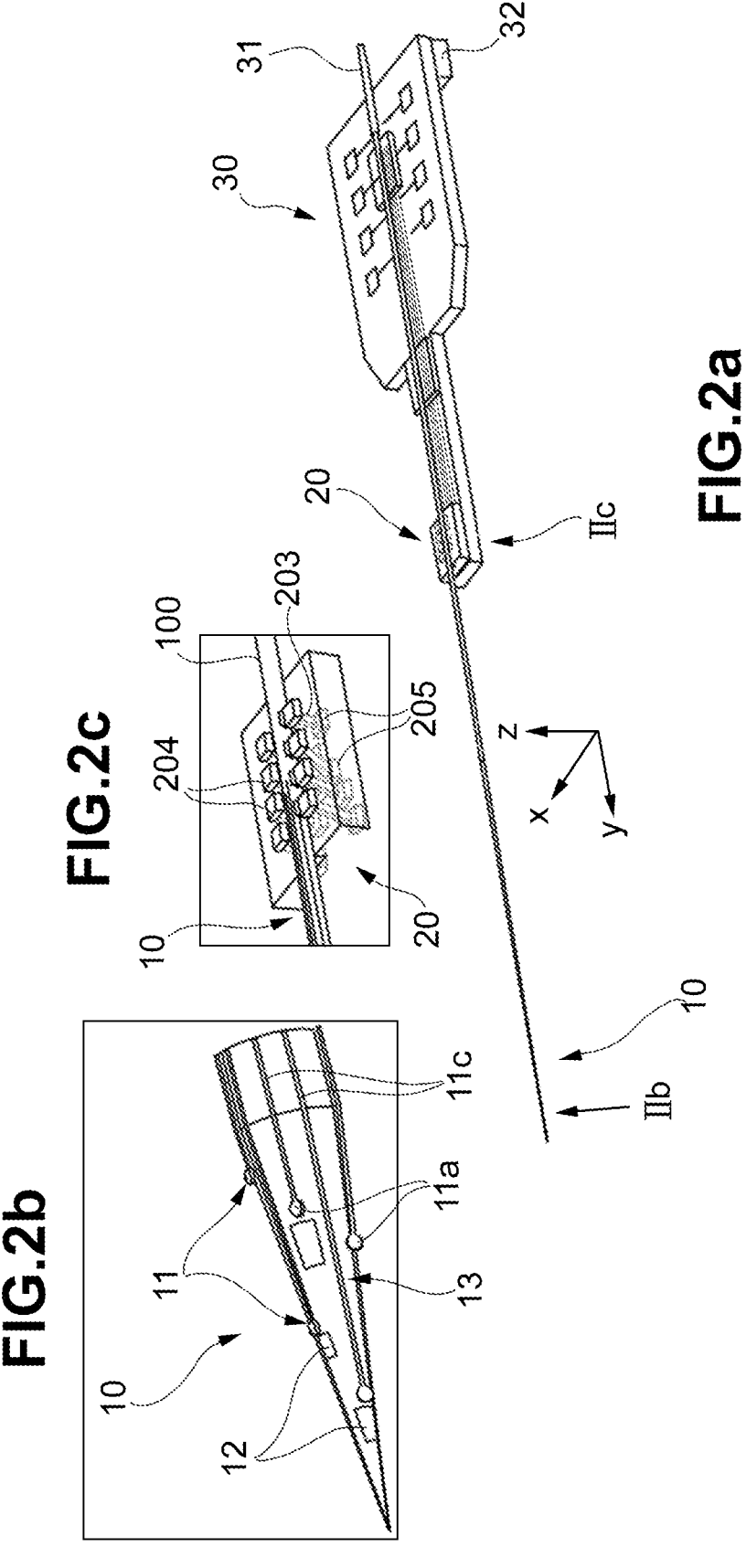
FIG. 2*a* is a schematic view of an optoelectronic device that may be produced using the method according to the invention.
FIGS. 2*b* and 2*c* are enlarged views of details respectively denoted by IIb and IIc in FIG. 2*a;*

The probe 10 is substantially an electromagnetic waveguide comprising a tapered optical fiber. FIG. 2*b* shows the tapering at the tip of the waveguide/optical fiber, which tapering is denoted by 13.

The fiber (and therefore the optical windows 12) receive and transmit light from/to external systems via a ferrule connection 31, while the signal collected by the electrodes 11 is sent to an external amplifier via a connector 32 on the planar board 30. Alternatively (as will be described below), the printed circuit interface 20 may be configured to send the signal collected by the electrodes 11 to an external amplifier via a connector integrated on the printed circuit interface 20, without the need for a planar board 30.

The optical windows 12 are used to distribute and/or collect light onto/from the tissue, while the electrodes 11 are used to detect nearby electric fields that are linked to cellular activity. Both of these are manufactured along and around the tapered section 13 using a multi-stage method shown in FIG. 3, which allows them to be produced despite the small and non-constant radius of curvature r(y), which may fall below 1 µm.

The method starts by mounting a tapered optical fiber 1 on a roto-translational handling apparatus RT which may be actuated to translationally move the optical fiber along at least one translation axis, preferably along three orthogonal axes x, y and z, and rotate the optical fiber 1 about a longitudinal axis thereof, which in the example coincides with the y-axis. The angle of rotation is denoted by 0 (FIG. 3(*i*)). By means of the apparatus RT, the tapered fiber 1 is submerged in a negative photoresist droplet D supported by a substrate S. The tapered section 13 of the fiber is then subjected to a two-photon polymerization (2PP) process; one or more fs-pulsed (femtosecond-pulsed) focused beams FB are scanned on the tapered section 13 (by controlling the movement of the tapered section by means of the apparatus RT) in order to form a polymer mask 41. The 2PP makes it possible to obtain a polymerization spot which has dimensions in the xy ($d_{xy}$) plane and along the z ($d_z$) direction below the diffraction limits, and therefore a smaller radius of curvature r(y) at the section in which the polymerization is carried out (i.e. $d_{xy} \ll r(y)$ e $d_z \ll r(y)$). Quantitatively, for a given dry and de, the minimum value of r(y) that may accommodate the mask formed using the 2PP process may be evaluated by solving the following equation:

$$\left( \sqrt{r^2(y) + \frac{d_{xy}^2}{4}} - r(y) \right) \cos\left( \tan^{-1} \frac{d_{xy}}{2r(y)} \right) = \frac{d_z}{4}. \tag{1}$$

Figure 3:
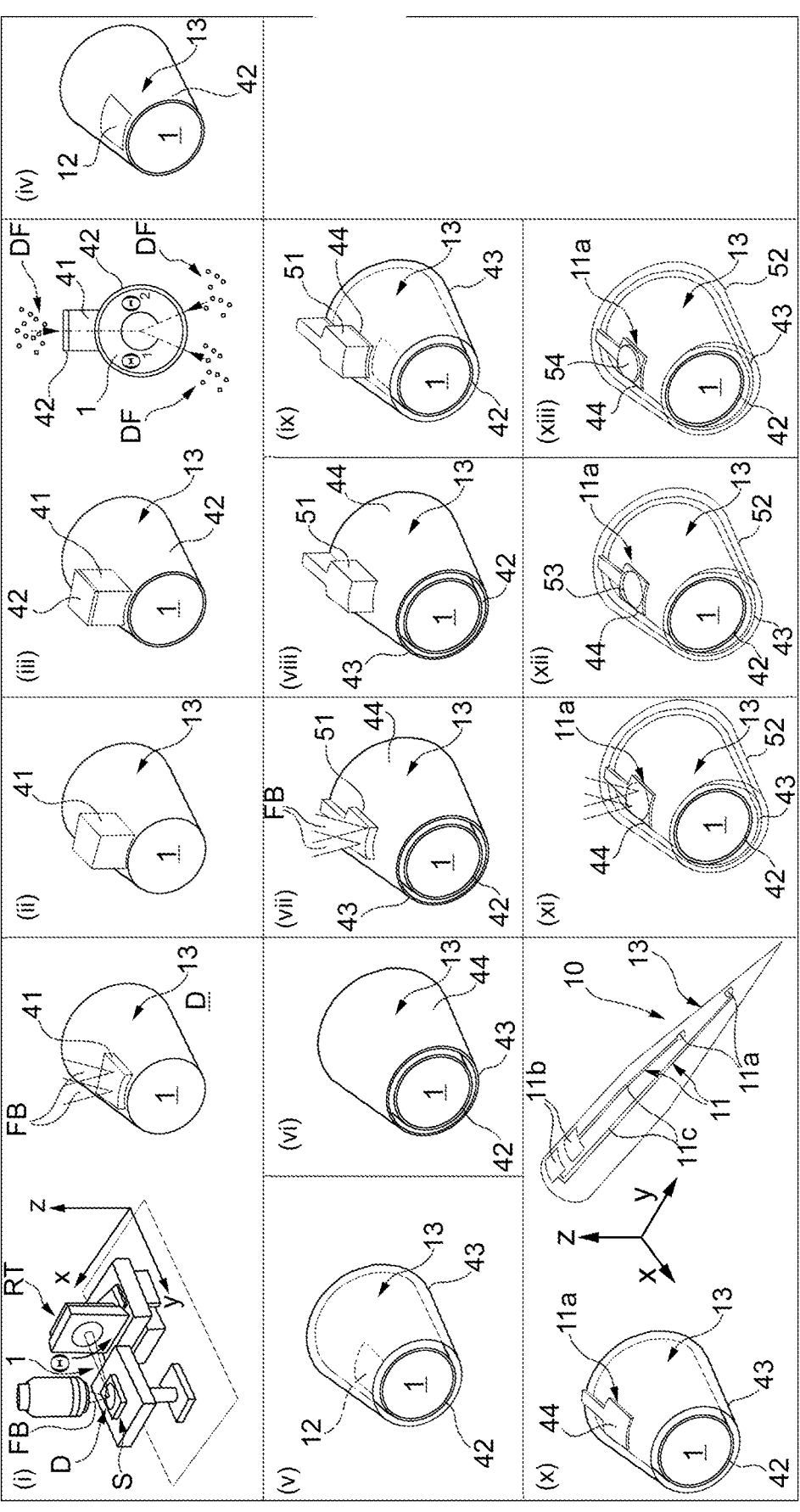
FIG. 3 shows the steps of a method for manufacturing a waveguide according to the invention.

This condition, together with the possibility of roto-translating the fiber 1 and scanning more beams, makes it possible to address the non-planarity of the tapered surface 13 and ensures good adhesion of the polymer structure 41 after the photoresist has been developed (FIG. 3(*ii*)).

The fiber is then placed in the chamber of a system for the directional evaporation of metals (for example an electron beam evaporator) and exposed to a plurality of different directional flows of metal (in the example, three flows DF), so as to cover the tapered section 13 with a first metal layer 42, while leaving the lateral edge of the mask 41 uncovered (FIG. 3(*iii*)). This is achieved by carrying out a plurality of different evaporations at different 0 angles, for example three different, separate evaporations at angles 01 and 02 which are equal to approximately 120°, but these values depend on the height and the shape of the structure(s) to be produced. The aspect ratio of the polymer mask 41 is generally greater than 1, in order to reduce the quantity of material deposited on the lateral surfaces of the mask (for example, for a square pattern of 15 µm×15 µm, the height may be ~20 µm).

With regard to the shape of the polymer mask 41, it is possible to produce square, rectangular or circular patterns, and, by properly controlling the laser focusing equipment, the shape may be freely defined while taking the limits of equation (1) into account.

Following the chemical removal of the photoresist mask 41, one or more optical windows 12 are obtained on the tapered section 13 (FIG. 3(iv)), which windows are formed through the first metal layer 42.

A transparent and conformal insulating layer 43 is then deposited, by means of chemical vapor deposition (for example of parylene-c) or electron beam evaporation (for example of silicon dioxide), as shown schematically in FIG. 3(v).

A second metal layer 44 is then deposited all around the fiber (FIG. 3(vi)), which second layer is used as a substrate for the electrical tracks.

The device is re-inserted into the photoresist droplet D and the 2PP is used to define a new photoresist mask 51 on the tapered surface 13, so as to define the geometry of one or more electrode contacts (FIG. 3(vii)). The method makes it possible to obtain masks of which the dimensions may vary from a few microns to centimeters.

The fiber is subjected to another development step (FIG. 3(viii)) and to subsequent wet etching in order to transfer the geometry of the photoresist to the metal layer 44 (FIG. 3(ix)). The photoresist is chemically removed (FIG. 3(x)), thus revealing the metal paths formed by measurement pads 11a (the shape of which may be circular or round, with dimensions that vary from a few micrometers to a few millimeters), connection pads 11b (dimensions from a few tens of micrometers to a few mm) and electrical tracks 11c (representative lengths from a few mm to a few cm, with transverse dimensions typically between a few microns and approximately 20 μm). The measurement pads 11a define the points at which the signal is detected by direct exposure to the electrolyte, while the connection pads 11b are used, in combination with the printed circuit interface 20, to interface the electrodes 11a, b, c with the planar printed circuit board 30.

The system is then insulated using a second transparent, conformal layer 52 made of polymer or semiconductor material, which layer also acts as a sealing encapsulation for the device in order to allow it to function in ambient liquids.

By means of single-photon or two-photon laser ablation, or by means of focused ion beam (FIB) abrasion (FIG. 3(xi)), a recess is 53 then formed in the second transparent layer 52 at the measurement pads 11a (FIG. 3(xii)). Then, by means of focused ion beam deposition or electrochemical deposition, a third metal layer 54 is deposited only in the recess 53 (FIG. 3(xiii)), with the aim of regulating the final impedance of the electrode to values in the range from 0.2 MΩ a 2 MΩ.

Figures 4A, 4B, 4C:
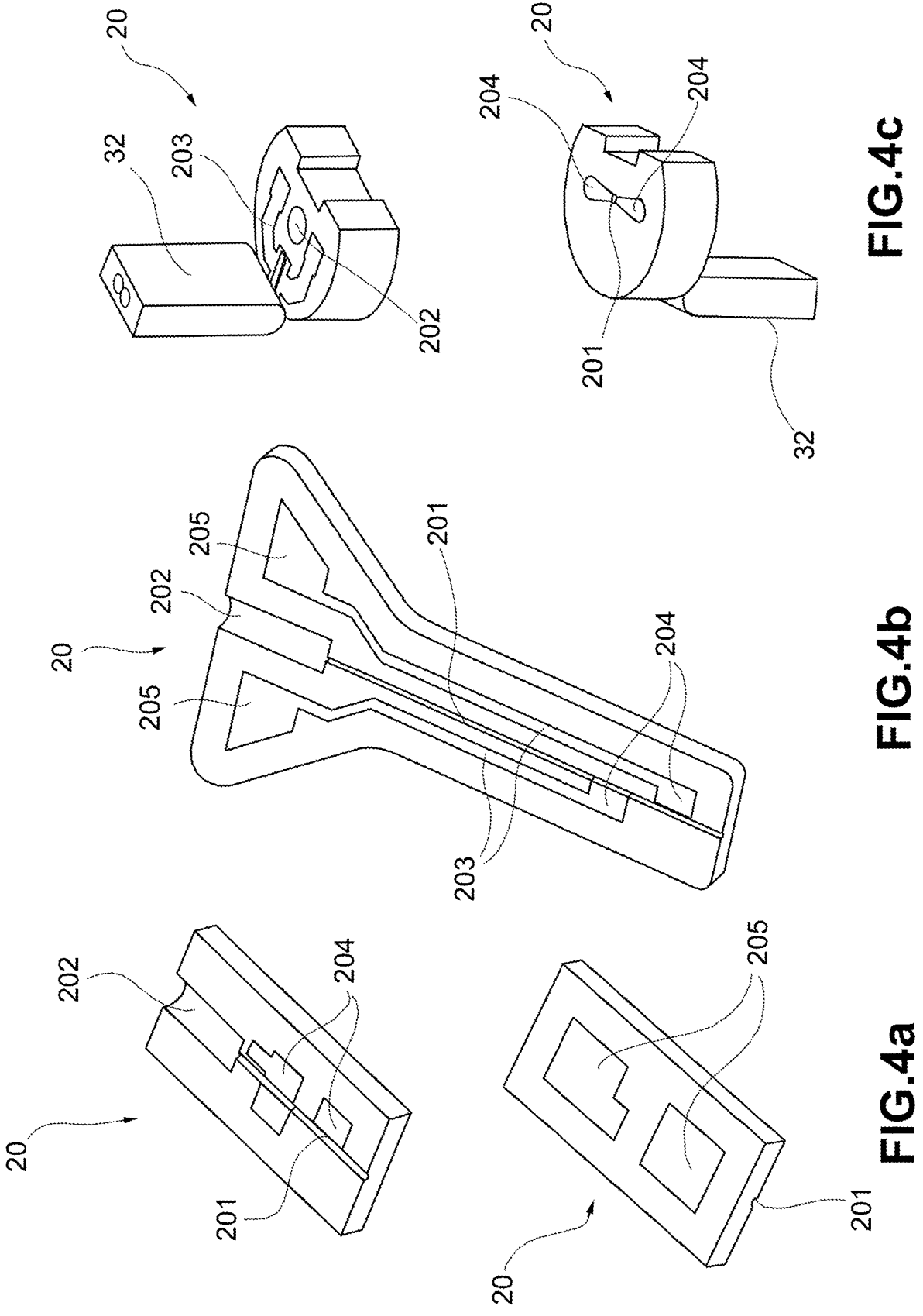
FIG. 4*a*-4*c* show different examples of a printed circuit interface for the waveguide in FIG. 3.

Between steps (x) and (xi), i.e. before the second transparent layer 52 is formed, the fiber 1 is removed from the handling apparatus RT and mounted on the printed circuit interface 20 which is specifically designed to interface the electrodes 11a, b, c to the planar board 30 for connection to an external amplification system. FIGS. 4a and 4b show two embodiments for the interface 20, each of which comprises a first seat 201 which is configured to receive the electromagnetic waveguide 10, and a second seat 202 which is aligned with the first seat 201 and configured to receive an optical cable 100 connected to the electromagnetic waveguide 10 (cf. also FIG. 2c). The interface 20 also comprises at least two conductive tracks 203, each of which comprises a distal connection pad 204 which faces the first seat 201 and is configured to be welded to a relevant connection pad 11b of one of the electrodes 11 of the electromagnetic waveguide 10, and a proximal connection pad 205 which is configured to be welded to a relevant contact of the planar board 30. FIG. 4a shows an example (similar to that in FIG. 2c) where the distal connection pads 204 are formed on an upper face of the interface 20 (shown at the top in FIG. 4a), and the proximal connection pads 205 are formed on a lower face of the interface 20 (shown at the bottom in FIG. 4a). The conductive tracks 203 which connect the distal connection pads 204 to the proximal connection pads 205 are formed through the thickness of the interface 20, as may be seen in FIG. 2c. FIG. 4b instead shows an example where the distal connection pads 204, proximal connection pads 205 and conductive tracks 203 are formed on the same face of the interface 20. As in the example in FIG. 2a-c, the printed circuit interface 20 is used to allow the electromagnetic waveguide 10 to be connected to a planar board 30, which is in turn responsible for connection to external amplifiers. FIG. 4c shows an alternative example where the printed circuit interface, again denoted by reference sign 20, acts as an independent interface with standard external systems, without the need for a planar board (the two images shown are views of the interface as seen from different directions). The example interface in FIG. 4c therefore has an integrated connector 32 for connection to external systems. In this case, the distal connection pads are directly connected to the connector 32.

Figure 5:
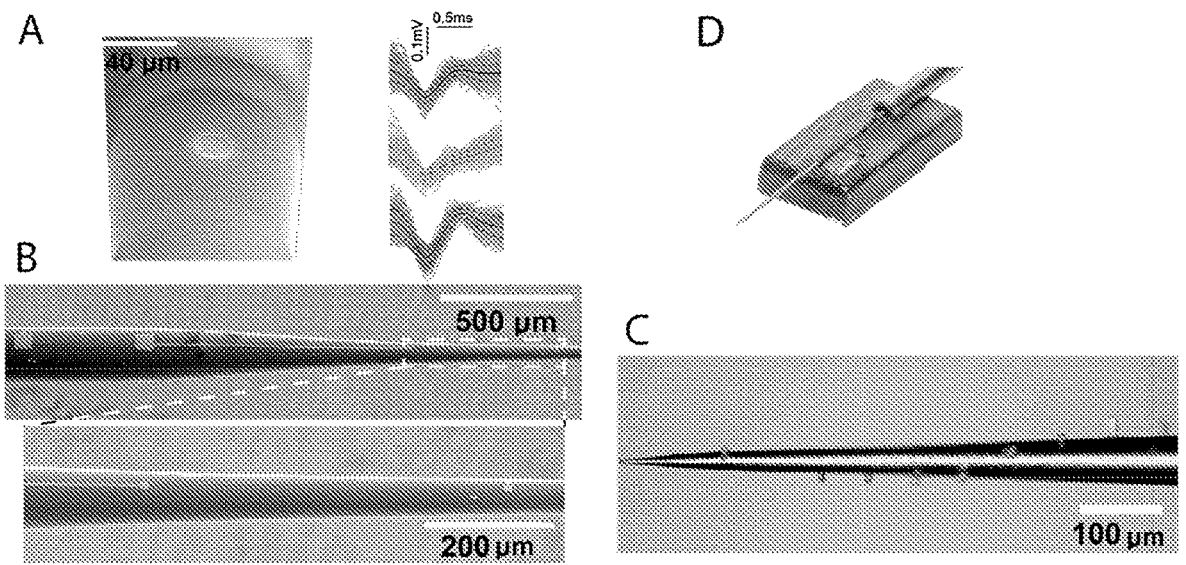
FIG. 5 shows images of prototypes obtained using the method according to the invention.

Preliminary results from the manufacturing method described above are shown in FIG. 5. Frame A shows a microscope image which shows a detail on an electrode obtained using the described method, and a graph relating to the action potentials recorded in vivo, in the cerebral tissue of a mouse, from three different cells. Frame B shows microscope images (at different magnifications) which show multiple electrodes formed on the same tip, which electrodes are composed of measurement pads, conductive tracks and connection pads. Frame C is a microscope image which shows polymer structures formed all around the tapered section, in order to demonstrate the suitability of the described approach for being used over the entire tapered surface. Frame D shows a photograph of a printed circuit interface produced using polymer materials, with a tapered and structured fiber mounted thereon and connected to an optical cable. This configuration corresponds to that in FIG. 4a, and may be welded to a planar board in order to interface with conventional amplifiers.

Figure 6:
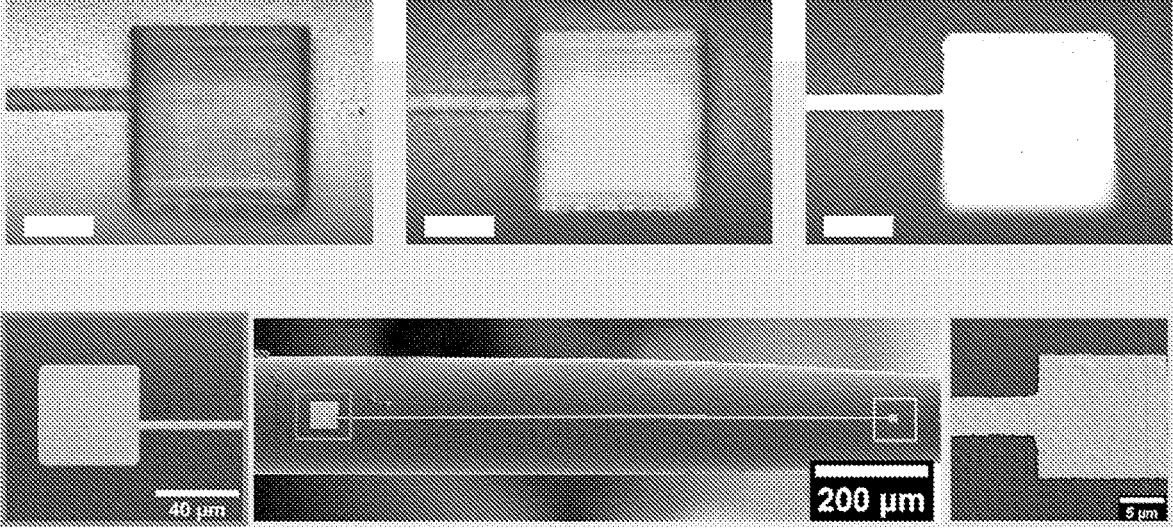
FIG. 6 shows images of test results relating to certain manufacturing steps of the method according to the invention.

FIG. 6 shows preliminary results relating to the crucial steps of the manufacturing method described above, i.e. the formation of the polymer masks and the transfer of their geometry onto the non-planar tapered surface. The three images at the top are microscope images which show a detail of the tip at the end of three different steps for forming a measurement pad, in particular:

image at the top left: after the development of the photoresist (step (viii))

image at the top center: after the chemical etching to remove the non-masked metal (step (ix))

image at the top right: after the removal of the photoresist (step (x)).

The three images at the bottom are microscope images of a conductive track formed on the tip, at different scales of magnification.

Bibliographical References

[1] Spagnolo, B et al. Integrated tapered fibertrode for simultaneous control and readout of neural activity over small brain volumes with reduced light-induced artefacts, *Bioarxiv* https://doi.org/10.1101/2020.07.31.226795 (2020)

[2] Pisano, F et al. Focused ion beam nanomachining of tapered optical fibers for patterned light delivery. *Microelectron. Eng.* 145, 41-49 (2018)

[3] Rizzo, A et al. Laser micromachining of tapered optical fibers for spatially selective control of neural activity. *Microelectron. Eng.* (2018) doi:10.1016/j.mee.2018.02.010.

[4] Balena, A et al. Two-photon fluorescence-assisted laser ablation of non-planar metal surfaces: fabrication of optical apertures on tapered fibers for optical neural interfaces. Opt. Express 28, 15, 21368-21381 (2020).

The invention claimed is:

1. A method for manufacturing a multifunctional electromagnetic waveguide from a tapered optical fiber, the method comprising:

mounting the optical fiber on a handling apparatus which may be actuated to translationally move the optical fiber along at least one translation axis and rotate the optical fiber about a longitudinal axis thereof, submerging a tapered section of the optical fiber in a photoresist and subjecting the photoresist to two-photon polymerization to form a first mask defining a shape of at least one optical window, subjecting the masked tapered section to a plurality of directional flows of metal material to form a first metal layer around the tapered section, leaving at least one lateral edge of the first mask uncovered, removing the first mask by chemical etching in such a way to uncover said at least one optical window, depositing a transparent, conformal first layer around the tapered section, said transparent, conformal first layer being made of insulating material, depositing a second metal layer around the insulating transparent, conformal first layer, submerging the tapered section in the photoresist and subjecting the photoresist to two-photon polymerization to form, at the tapered section, a second mask defining a shape of at least one conductive track, removing, by chemical etching, the second metal layer where the second metal layer is not covered by the second mask, and removing the second mask by chemical etching in such a way to uncover said at least one conductive track.

2. The method of claim 1, further comprising depositing a transparent, conformal second layer around the tapered section, said transparent, conformal second layer being made of polymer or semiconductor material.

3. The method of claim 2, further comprising forming at least one recess at at least one measurement pad of said at least one conductive track, and depositing a third metal layer in said at least one recess.

4. The method claim 1, further comprising mounting the multifunctional electromagnetic waveguide on a printed circuit interface, said printed circuit interface comprising a first seat configured to receive the multifunctional electromagnetic waveguide, a second seat aligned with the first seat and configured to receive an optical cable connected to the multifunctional electromagnetic waveguide, and at least one conductive track comprising a distal connection pad facing the first seat and configured to be welded to a relevant connection pad of said at least one conductive track of the multifunctional electromagnetic waveguide.

5. The method of claim 1, wherein, during the two-photon polymerization, the optical fiber is rotated around its longitudinal axis by the handling apparatus.

* * * * *